(12) United States Patent
Barrett et al.

(10) Patent No.: US 9,658,172 B2
(45) Date of Patent: May 23, 2017

(54) METHOD OF INSPECTING A PART USING A MARKING TEMPLATE FOR RADIOGRAPHY

(71) Applicant: PCC Structurals, Inc., Portland, OR (US)

(72) Inventors: James Raphord Barrett, Milwaukie, OR (US); Jason Armstrong, Oregon City, OR (US); Doug Nikolas, Battle Ground, WA (US); Andrew Isaac Deceuster, Oregon City, OR (US); Lawrence Lang, Portland, OR (US)

(73) Assignee: PCC STRUCTURALS, Portland, OR (US)

( * ) Notice: Subject to any disclaimer, the term of this patent is extended or adjusted under 35 U.S.C. 154(b) by 0 days.

(21) Appl. No.: 14/991,179

(22) Filed: Jan. 8, 2016

(65) Prior Publication Data

US 2016/0123903 A1    May 5, 2016

Related U.S. Application Data

(62) Division of application No. 13/827,895, filed on Mar. 14, 2013, now Pat. No. 9,275,769.

(51) Int. Cl.
| | | |
|---|---|---|
| *G01N 23/04* | (2006.01) | |
| *G21K 1/00* | (2006.01) | |
| *B29C 67/00* | (2017.01) | |
| *G21K 1/10* | (2006.01) | |
| *A61B 6/12* | (2006.01) | |

(52) U.S. Cl.
CPC .......... *G01N 23/04* (2013.01); *B29C 67/0055* (2013.01); *B29C 67/0077* (2013.01); *G21K 1/00* (2013.01); *G21K 1/10* (2013.01); *A61B 6/12* (2013.01); *G01N 2223/417* (2013.01); *G01N 2223/646* (2013.01); *Y10T 29/49* (2015.01); *Y10T 29/49718* (2015.01)

(58) Field of Classification Search
CPC ... A61B 6/12; B29C 67/0077; B29C 67/0055; G01N 23/04; G01N 2223/646; G01N 2223/417; G21K 1/00; G21K 1/10; Y10T 29/49; Y10T 29/49718
See application file for complete search history.

(56) References Cited

U.S. PATENT DOCUMENTS

| | | | | |
|---|---|---|---|---|
| 3,547,121 A | * | 12/1970 | Cherry | A61M 5/427 378/164 |
| 3,573,455 A | * | 4/1971 | Suierveld | G01N 23/04 156/64 |

(Continued)

FOREIGN PATENT DOCUMENTS

| | | | | |
|---|---|---|---|---|
| WO | WO 9013258 A1 | * | 11/1990 | A61B 6/12 |

*Primary Examiner* — Jermie Cozart
(74) *Attorney, Agent, or Firm* — Burris Law, PLLC

(57) ABSTRACT

A method of inspecting a part is provided that includes the steps of aligning a contoured sheet having at least one surface that corresponds to at least one surface of the part, the contoured sheet having first portions and second portions, the first portions being radiodense and the second portions being radiolucent, and at least some of the second portions corresponding to internal features of the part. The part with the contoured sheet is exposed to x-rays to produce a first radiograph with markings that correspond to the first and second portions of the contoured sheet.

17 Claims, 4 Drawing Sheets

(56) References Cited

U.S. PATENT DOCUMENTS

| | | | | |
|---|---|---|---|---|
| 3,742,230 A * | 6/1973 | Spears | G03F 1/22 | |
| | | | 216/12 | |
| 3,952,194 A * | 4/1976 | Bayonnet | G01N 23/185 | |
| | | | 378/163 | |
| 4,349,917 A * | 9/1982 | Moore | A61B 6/4283 | |
| | | | 378/164 | |
| 4,860,331 A * | 8/1989 | Williams | A61B 6/08 | |
| | | | 116/278 | |
| 4,918,715 A * | 4/1990 | Krupnick | A61B 6/12 | |
| | | | 378/162 | |
| 4,985,019 A * | 1/1991 | Michelson | A61B 6/12 | |
| | | | 128/DIG. 26 | |
| 5,052,035 A * | 9/1991 | Krupnick | A61B 6/08 | |
| | | | 378/162 | |
| 5,299,253 A * | 3/1994 | Wessels | A61B 6/5235 | |
| | | | 378/163 | |
| 5,799,059 A * | 8/1998 | Stembridge | A61B 6/583 | |
| | | | 378/18 | |
| 6,269,148 B1 * | 7/2001 | Jessop | G01N 23/04 | |
| | | | 378/162 | |
| 6,289,235 B1 * | 9/2001 | Webber | A61B 6/12 | |
| | | | 378/23 | |
| 6,315,445 B1 * | 11/2001 | Mazess | A61B 6/4225 | |
| | | | 348/E3.045 | |
| 6,333,970 B1 * | 12/2001 | LeMaitre | A61B 5/411 | |
| | | | 378/162 | |
| 6,658,089 B1 * | 12/2003 | Mohr | G01N 23/04 | |
| | | | 378/162 | |
| 6,928,146 B2 * | 8/2005 | Broyles | A61B 6/12 | |
| | | | 378/163 | |
| 7,065,176 B2 * | 6/2006 | Moermond | G01N 23/04 | |
| | | | 378/58 | |
| 8,021,150 B2 * | 9/2011 | Fuentevilla | A61C 1/084 | |
| | | | 433/173 | |
| 9,275,769 B2 * | 3/2016 | Barrett | G21K 1/00 | |
| 2006/0251220 A1 * | 11/2006 | Young | A61C 1/084 | |
| | | | 378/204 | |
| 2006/0257817 A1 * | 11/2006 | Shelton | A61C 8/0089 | |
| | | | 433/75 | |
| 2009/0304155 A1 * | 12/2009 | Davis | G01N 23/04 | |
| | | | 378/98.5 | |
| 2011/0019796 A1 * | 1/2011 | Wuestenbecker | G01N 23/046 | |
| | | | 378/20 | |
| 2014/0259588 A1 * | 9/2014 | Barrett | G21K 1/00 | |
| | | | 29/402.01 | |
| 2016/0123903 A1 * | 5/2016 | Barrett | G21K 1/00 | |
| | | | 378/58 | |

\* cited by examiner

METHOD OF INSPECTING A PART USING A MARKING TEMPLATE FOR RADIOGRAPHY

CROSS-REFERENCE TO RELATED APPLICATIONS

This application is a divisional of and claims the benefit to U.S. patent application Ser. No. 13/827,895, filed on Mar. 14, 2013, now U.S. Pat. No. 9,275,769; issued Mar. 1, 2016 the entire contents of which are incorporated herein by reference in their entirety.

FIELD

This disclosure relates generally to radiography of parts. More specifically, this disclosure relates to radiography of castings to locate defects.

BACKGROUND

The statements in this section merely provide background information related to the present disclosure and may not constitute prior art.

Defects in castings can form as a result of the casting process. Internal defects may not be found from merely inspecting the surface of the casting. Therefore, radiography is often used to inspect castings in order to identify and locate internal defects that a casting may have.

Radiography includes exposing the casting to x-rays in order to produce a radiograph. The radiograph can be reviewed to see if the casting has any defects. However, accurately locating the defects in the casting that are found on the radiograph can be difficult. For example, the radiograph may be a different size than the casting. Furthermore, the orientation of the casting when the radiograph was taken may be difficult to determine.

In order to more accurately locate internal defects of a casting, lead indicators can be taped to the casting. However, numerous radiographs may need to be taken when using lead indicators. A first radiograph is typically taken without any lead indicators taped to the casting. Lead indicators may then be taped to the casting around where the defects are believed to be located, and a second radiograph can be taken. Therefore, more than one radiograph is typically needed to accurately identify locations of defects.

An additional radiograph can also be taken with lead indicators in the area of the defect to perform a parallax shot with the intent of determining the defects relative depth. Parallax principles and methods are further described in Barry, R. and Ruescher, E., "Stereo Radiography," Nondestructive Testing Handbook, third edition, Vol. 4, Radiographic Testing, Columbus, Ohio, American Society for Nondestructive Testing (2002), p 419-423.

After defect locations are identified, the defect locations of the casting can be reworked or remedied. Although the methods described above can identify locations of defects, at least two radiographs typically need to be taken of the casting in order to obtain an accurate location of the defects which can add cost and complexity to the inspection process of the casting.

SUMMARY

According to one aspect of the present disclosure, a method of inspecting a part is provided. The method includes aligning a contoured sheet having at least one surface that corresponds to at least one surface of a first target part. The contoured sheet has first portions and second portions. The first portions are radiodense and the second portions are radiolucent. The method further includes exposing the first target part with the contoured sheet to x-rays to produce a first radiograph with markings that correspond to the first and second portions.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figures 1, 2:
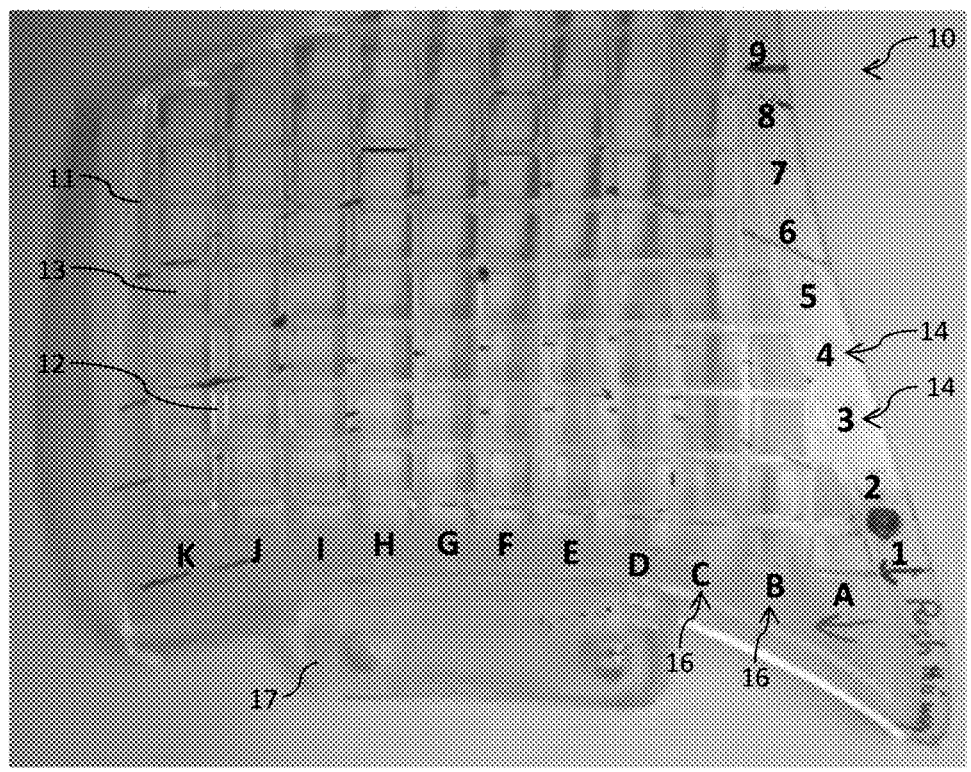
FIG. 1 is an example of a template for radiography compatible with certain aspects of the present disclosure.
FIG. 2 is a radiograph of a template on a casting.

The following description is merely exemplary in nature and is in no way intended to limit the present disclosure or its application or uses. It should be understood that throughout the description, corresponding reference numerals indicate like or corresponding parts and features.

The present disclosure generally relates to templates for radiography of parts. The templates made and used according to the teachings contained herein are described through the present disclosure in conjunction with castings in order to more fully illustrate the concept. The use of the template in conjunction with other types of parts and components is contemplated to be within the scope of the disclosure.

According to certain aspects of the present disclosure, a template for radiography is provided. FIG. 1 illustrates an example template 10 for inspecting a casting such as a strut. The template 10 includes a contoured sheet 11 having first portions 12 and second portions 13. The first portions 12 are radiodense and the second portions 13 are radiolucent to provide markings on a radiograph.

At least one surface of the contoured sheet 11 corresponds to at least one surface of a target part to provide alignment of the contoured sheet 11 to the target part. Having a surface of the contoured sheet 11 correspond to a surface of the target part can allow for positioning the contoured sheet 11 onto the target part to be consistent each time. For instance, the contoured sheet 11 can effectively be self-aligning to the target part when positioned onto the target part. Furthermore, the positioning of the contoured sheet 11 onto different target parts that are similar or substantially identical can be consistent between the different target parts.

The portions that are radiodense have a radiopacity (e.g., amount of x-ray radiation that does not pass through the portions) greater than the radiopacity of the portions that are radiolucent. For example, the portions that are radiodense can be at least partially radiopaque to x-ray radiation, and the portions that are radiolucent can be completely or almost completely transparent to x-ray radiation. For instance, the portions that are radiolucent (e.g., the second portions 13) can be openings through the contoured sheet 11.

The first portions 12 and the second portions 13 of the contoured sheet 11 can form a grid of alternating first and second portions 12, 13 along the contoured sheet 11. Furthermore, the grid can have rows 14 and columns 16 of alternating first and second portions 12, 13. The first and second portions 12, 13 can be regularly spaced or irregularly spaced. The first and second portions 12, 13 can have orthogonal shapes such as rectangles or squares, or have other non-orthogonal shapes such as corresponding internal feature of the target part (discussed below). The rows 14 and columns 16 can be labeled to be identifiable. For example, as illustrated in FIG. 1, the rows 14 are labeled with numerical characters and the columns 16 are labeled with alphabetical characters. However, other characters and labeling are also contemplated.

The contoured sheet 11 can be at least partially transparent to visible light. By having the contoured sheet 11 capable of having visible light transmit through the contoured sheet 11, the surface of the target part adjacent to the contoured sheet 11 can be viewed. For example, if the second portions 13 include openings, the openings can allow visible light to pass through the contoured sheet 11. In addition or alternatively, the first portions 12 can be made of a material that is transparent or at least partially transparent to visible light.

Figure 3:
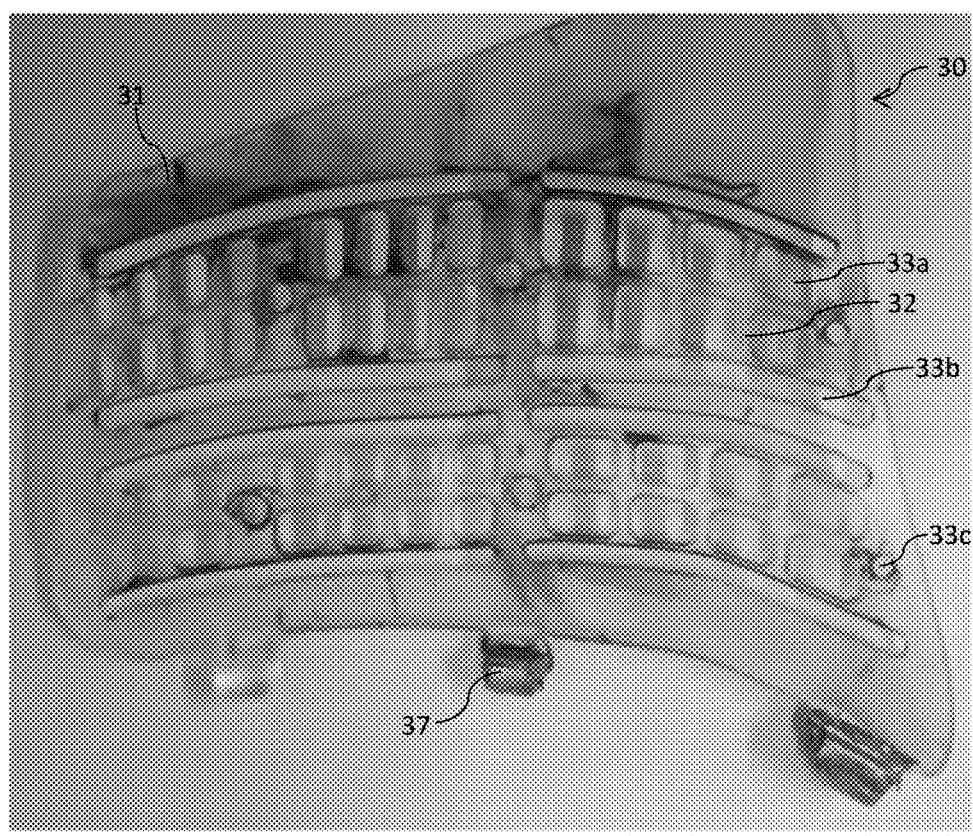
FIG. 3 is another example of a template for radiography compatible with certain aspects of the present disclosure having features on the contoured sheet that correspond to internal features of a target part.

The template 10 can further include fasteners to removably couple the contoured sheet 11 to the target part. For example, as illustrated in FIG. 1, the template 10 includes pins 17 that align the contoured sheet 11 to the target part. FIG. 3 shows another example template 30 that includes locators 37 that wrap at least partially around the target part to further assist in aligning the contoured sheet 31 to the target part.

FIG. 3 illustrates another example of a template 30. The template 30 is similar to the template 10 of FIG. 1 in that the template 30 includes a contoured sheet 31 that has first portions 32 and second portions 33. At least some of the second portions 33 can correspond to internal features of the target part. For example, the internal features can include at least one internal feature selected from the group consisting of core passages and core support holes. The second portion 33b, in FIG. 3, is an example of a second portion that corresponds to a feature of the part. Another second portion 33c is an example of a second portion that corresponds to a core support hole of the part. The second portions 33 that correspond to internal features can have dimensions that correspond to dimensions of the internal features. In particular, the second portions 33 that correspond to internal features can neighbor the internal features when the contoured sheet 31 is aligned to the target part.

As discussed above, at least one surface of the contoured sheet 11, 31 corresponds to at least one surface of a target part to provide alignment of the contoured sheet 11, 31 to the target part. For instance, the template may be form fitting to the target part. The at least one surface of the contoured sheet 11, 31 can correspond to or match the topography of the at least one surface of the target part. Therefore, the at least one surface of the contoured sheet 11, 31 can have sections that are flat and/or curved. In one example, the at least one surface of the contoured sheet 11, 31 can be a B-surface. In another example, the at least one surface of the contoured sheet 11, 31 is flat.

Furthermore, to assist in placement of the template 10, 30 onto the part, the template 10, 30, in addition to having a surface that corresponds to the surface of the target part, can be of a general shape that corresponds to the target part. For example, an outer perimeter of the template 10, 30 may have a shape that corresponds to an outer surface of the target part when the template 10, 30 positioned correctly onto the target part.

Figure 4:
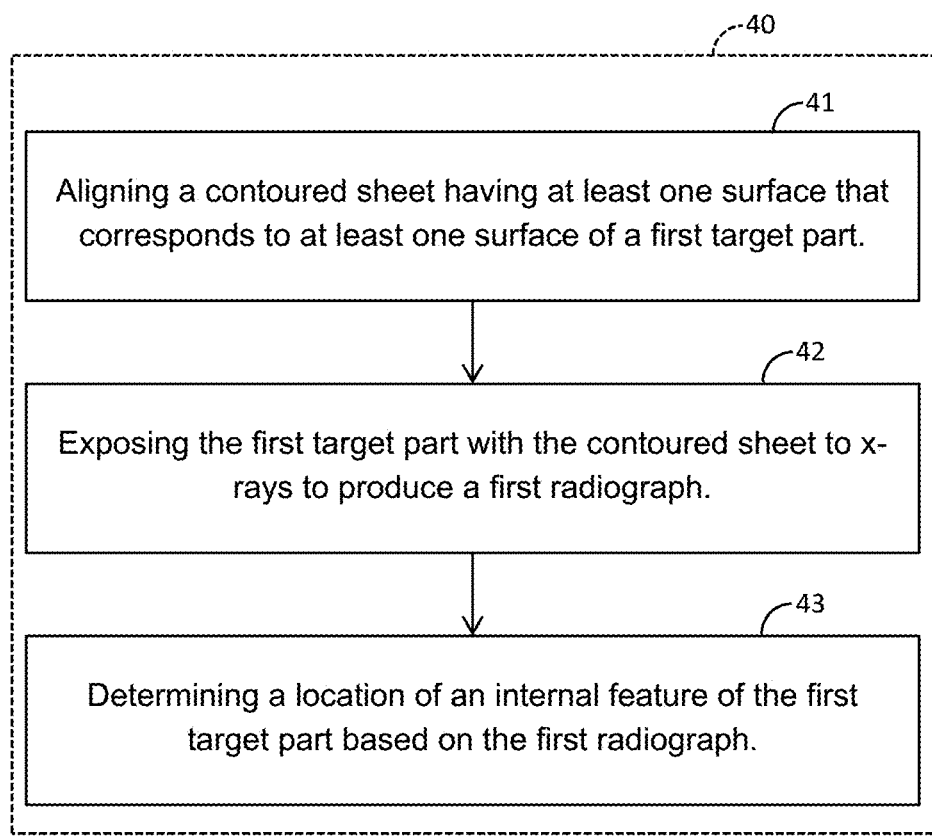
FIG. 4 is a flow diagram of an example method of using a template compatible with certain aspects of the present disclosure.

The above described templates can be used in a number of methods to inspect target parts. FIG. 4 is a flow diagram of an example method 40 compatible with certain aspects described herein. In operational block 41, the method can include aligning a contoured sheet 11, 31 having at least one surface that corresponds to at least one surface of a first target part. The contoured sheet 11, 31 has first portions 12, 32 that are radiodense and second portions 13, 33 that are radiolucent.

In operational block 42, the method 40 can further include exposing the first target part with the contoured sheet 11, 31 to x-rays to produce a first radiograph with markings that correspond to the first 12, 32 and second 13, 33 portions. FIG. 2 is an example radiograph that was taken of a target part with a template 20 positioned on the target part. The template 20 is similar to that of the template 10 of FIG. 1. The first portions 12 and the second portions 13 of the contoured sheet 11 result in a grid of lighter portions 22 and darker portions 23, respectively, on the radiograph.

In operational block 43, the method 40 can further include determining a location of an internal feature of the first target part based on the first radiograph. The internal feature of the first target part can include a defect such as porosity, inclusion, etc. For instance, the method can further include repairing the defect. Repairing the defect can include removing the defect from the first target part and welding a region of the first target part where the defect was removed. The internal feature of the first target part can also be nondefects such as core passages and core support holes. For example, a core support hole 28 can be seen in the radiograph of FIG. 2 as round holes. However, the internal feature can include other nondefects as discussed herein.

As shown in FIG. 2, the radiodense portions can allow a portion of the x-rays to pass through so that internal features can still be seen in the radiograph even if they are behind the radiodense portions. Therefore, only a single radiograph may need to be taken of the target part to accurately locate internal features. However, if the radiodense portions blocks enough x-rays so that internal features are blocked by the radiodense portions, a second radiograph can be produced without the template. For instance, a method of inspecting a part can include exposing the first target part without the contoured sheet 11, 31 to x-rays to produce a second radiograph. The first radiograph can be compared to the second radiograph. For example, the first radiograph and the second radiograph can be overlaid with one another so that the image of the first target part of the first radiograph is aligned with the image of the first target part of the second radiograph. The markings that correspond to the first and second portions of the first radiograph can be used to locate internal features of the first target part.

Figure 5:
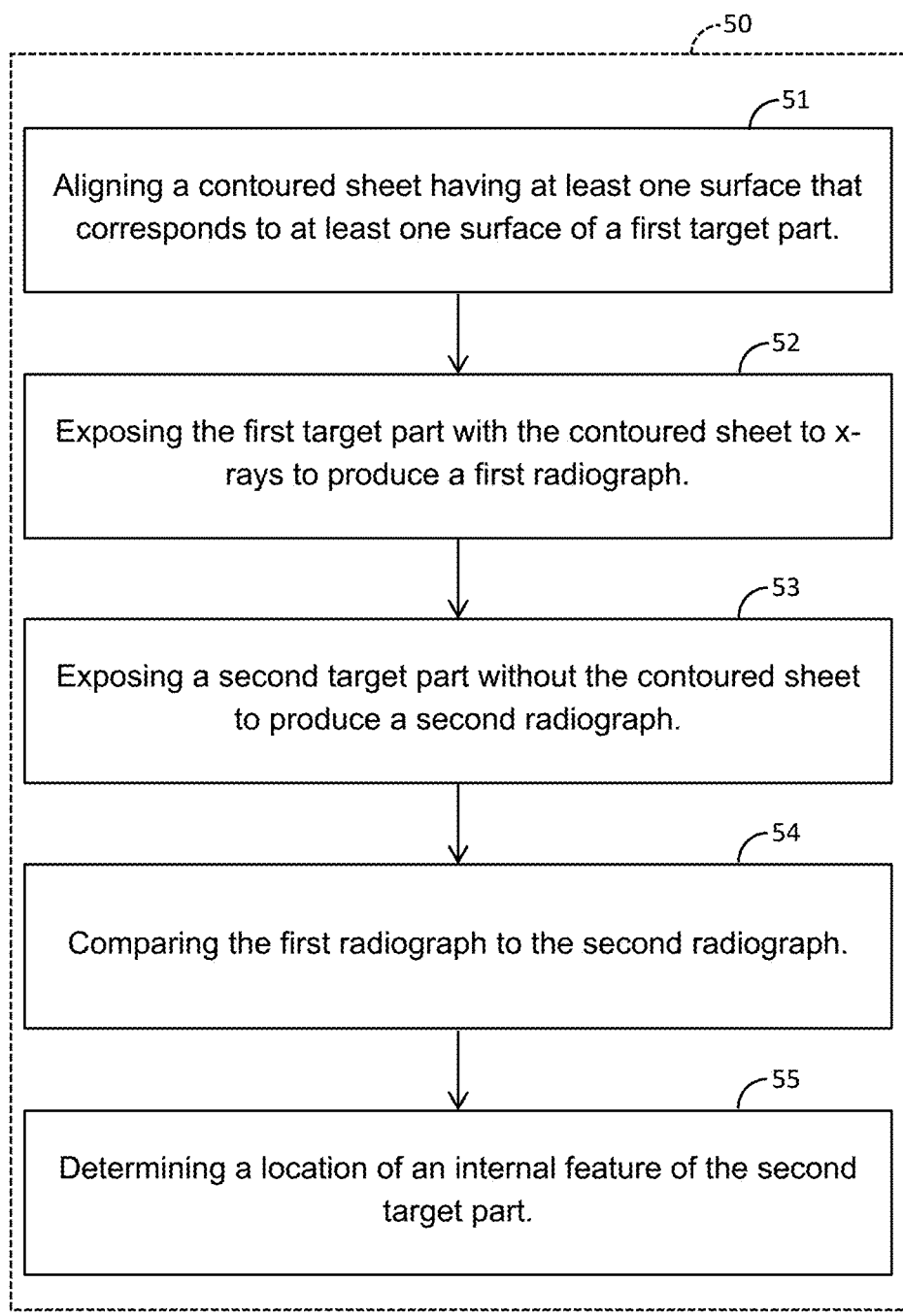
FIG. 5 is a flow diagram of another example method of using a template compatible with certain aspects of the present disclosure.

FIG. 5 is a flow diagram of another example method 50 compatible with certain aspects described herein. In operational blocks 51 and 52, the method can include aligning a contoured sheet having at least one surface that corresponds to at least one surface of the first target part and exposing the first target part with the contoured sheet to x-rays to produce a first radiograph, respectively. Operational blocks 51 and 52 can also include additional features such as those discussed above with regarding to operational blocks 41 and 42 of FIG. 4.

In operational block 53, the method 50 can include exposing a second target part to x-rays without the contoured sheet 11, 31 to produce a second radiograph. For example, the second target part may be exposed to x-rays without a template or other means for producing markings on a radiograph. The second target part can be dimensionally similar or substantially identical to the first target part.

In operational block 54, the method can include comparing the first radiograph to the second radiograph. The first and second radiographs can be compared because the first and second target parts are dimensionally similar.

In operational block 55, the method can include determining a location of an internal feature of the second target part. The first radiograph and the second radiograph can be overlaid with one another so that the image of the first target part of the first radiograph is aligned with the image of the second target part of the second radiograph. The markings that correspond to the first and second portions of the first radiograph can be used to locate internal features of the second target part.

Parallax principles can be used together with the methods described above to more accurately determine a location of an internal feature. The exposing of the first target part with the contoured sheet to x-rays can be performed at a first angle relative to the first target part. The method can further include exposing the first target part with or without the contoured sheet to x-rays at a second angle relative to the first target part that is different than the first angle. By producing radiographs from more than one position or line of sight relative to the target part and using the angle between the positions, the depth can be calculated of an internal feature in the target part. Determining the depth of an internal feature can particularly beneficial when the target part has a relatively thick section.

The templates described herein can be formed from various materials and can be manufactured by a variety of methods. The templates can be formed from materials such as polymers and metals. Furthermore, the templates can be a composite with the first portions that are radiodense formed of a first material and the second portions that are radiolucent formed of a second material, and the radiopacity of the first material can be greater than the radiopacity of the second material. The thickness of the contoured sheet can be relatively less than the other overall dimensions of the template. The thickness can be selected such that the contoured sheet has sufficient stiffness to maintain the contours based on the selected material that the template is formed thereof. However, the contoured sheet may be able to be elastically deformed some in order to attach the template to the target part.

As described above, the second portions that are radiolucent can be openings or voids that extend through the template. In an example method of manufacturing a template for radiography, the method can include forming a contoured sheet 11, 31 with openings having at least one surface that corresponds to at least one surface of a target part. The contoured sheet 11, 31 can comprise a material that is radiodense such that the radiodense material and openings are configured to provide markings on a radiograph.

The forming the contoured sheet can be by an additive manufacturing process. For example, the additive manufacturing process can be by stereolithography, selective laser sintering, fused deposition modeling, or large area maskless photopolymerization.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of inspecting a target part, the method comprising:
   aligning a contoured sheet having at least one surface that corresponds to at least one surface of the target part, the contoured sheet having first portions and second portions, the first portions being radiodense and the second portions being radiolucent, and at least some of the second portions corresponding to internal features of the target part; and
   exposing the target part with the contoured sheet to x-rays to produce a first radiograph with markings that correspond to the first and second portions.

2. The method of claim 1, further comprising determining a location of an internal feature of the target part based on the first radiograph.

3. The method of claim 2, wherein the internal feature is at least one of a core passage and a core support hole.

4. The method of claim 2, wherein the internal feature of the target part comprises a defect.

5. The method of claim 4, further comprising repairing the defect.

6. The method of claim 5, wherein the repairing the defect comprises removing the defect from the target part and welding a region of the target part where the defect was removed.

7. The method of claim 1, further comprising comparing the first radiograph to a second radiograph of a second target part that is dimensionally similar to that of the target part.

8. The method of claim 1, further comprising exposing a second target part without the contoured sheet to x-rays to produce a second radiograph, the second target part dimensionally similar to the target part; and comparing the first radiograph to the second radiograph.

9. The method of claim 1, further comprising exposing the target part without the contoured sheet to x-rays to produce a second radiograph.

10. The method of claim 9, wherein the first radiograph is compared to the second radiograph to locate internal features of the first target part.

11. The method of claim 10, wherein the first radiograph and the second radiograph are be overlaid with one another such that an image of the first target part of the first radiograph is aligned with an image of the first target part of the second radiograph.

12. The method of claim 1, further comprising elastically deforming the contoured sheet.

13. The method of claim 1, further comprising determining a depth of an internal feature within the target part.

14. The method of claim 13, wherein the exposing the first target part with the contoured sheet to x-rays is performed at a first angle relative to the first target part, and exposing the first target part with the contoured sheet to x-rays at a second angle relative to the first target part that is different than the first angle.

15. The method of claim 1, wherein the target part defines contours and wherein a thickness of the contoured sheet is selected to maintain the contours of the target part.

16. The method of claim 1, wherein the contoured sheet is a polymer material.

17. The method of claim 1, wherein the contoured sheet is a composite material and the first portions that are radiodense are formed of a first material and the second portions that are radiolucent are formed of a second material, and the radiopacity of the first material is greater than the radiopacity of the second material.

\* \* \* \* \*